United States Patent [19]

Peterson et al.

[11] Patent Number: 5,370,864
[45] Date of Patent: * Dec. 6, 1994

[54] BREATH PROTECTION MICROCAPSULES

[75] Inventors: Liezl G. Peterson, Cincinnati; Lowell A. Sanker, Montgomery; James G. Upson, Springdale, all of Ohio

[73] Assignee: The Procter & Gamble Company, Cincinnati, Ohio

[*] Notice: The portion of the term of this patent subsequent to Feb. 15, 2011 has been disclaimed.

[21] Appl. No.: 85,222

[22] Filed: Jun. 29, 1993

[51] Int. Cl.$^5$ ............ A61K 9/50; A61K 9/16; A61K 9/68

[52] U.S. Cl. ............ 424/49; 424/435; 424/440; 424/490; 514/948; 514/963

[58] Field of Search ............ 424/49-58, 424/435, 440, 490; 514/948, 963

[56] References Cited

U.S. PATENT DOCUMENTS

| | | | |
|---|---|---|---|
| 2,446,792 | 8/1948 | Shelton et al. | 260/295 |
| 3,431,208 | 3/1969 | Bailey | 252/106 |
| 3,832,460 | 8/1974 | Kosti | 424/54 |
| 3,911,099 | 10/1975 | DeFoney et al. | 424/28 |
| 4,039,653 | 8/1977 | DeFoney et al. | 424/19 |
| 4,158,068 | 6/1979 | Von Rymon Lipinski et al. | 426/548 |
| 4,251,195 | 2/1981 | Suzuki et al. | 425/6 |
| 4,312,889 | 1/1982 | Meisheimer | 426/86 |
| 4,422,985 | 12/1983 | Morishita et al. | 264/4.4 |
| 4,426,337 | 1/1984 | Suzuki et al. | 264/4 |
| 4,481,157 | 11/1984 | Morishita et al. | 264/4.1 |
| 4,695,466 | 9/1987 | Morishita et al. | 424/456 |
| 4,765,984 | 8/1988 | Vellekoop et al. | 424/441 |
| 5,004,595 | 4/1991 | Cherukuri et al. | 424/48 |
| 5,008,106 | 4/1991 | Merianos et al. | 424/80 |

FOREIGN PATENT DOCUMENTS 0332175 9/1989 European Pat. Off. .

*Primary Examiner*—Shep K. Rose
*Attorney, Agent, or Firm*—D. K. Dabbiere; D. C. Mohl; J. C. Rasser

[57] ABSTRACT

The present invention relates to oral compositions in the form of microcapsules which reduce oral bacteria and provide long lasting breath protection.

16 Claims, No Drawings

BREATH PROTECTION MICROCAPSULES

TECHNICAL FIELD

The present invention relates to oral compositions in the form of microcapsules which reduce oral bacteria and provide long lasting breath protection.

BACKGROUND OF THE INVENTION

The use of breath control compositions such as breath mints, mouthwashes, chewing gums, etc. is widespread in most of the developed countries of the world. Another form which has been used are microcapsules containing a flavorant or other breath protection agent. These executions have acceptance due not only to their usefulness away from a place to expectorate mouthwashes but also due to the fact that they can be swallowed when the user does not need any more of the actives or doesn't want the microcapsule in the mouth any longer.

Although microcapsules have been used, there are problems associated with incorporating certain breath protection agents/antimicrobials into the core. Oftentimes the wall of the microcapsule may develop imperfections and cause loss of the contents prematurely. Additionally, the actives may not be easily solubilized in the materials usually present in the core.

The prior art discloses a variety of means for providing breath protection and reducing oral bacteria. Included among such means are sprays disclosed in U.S. Pat. No. 3,431,208, Mar. 4, 1969 to Bailey. Particles containing an adhesive member are disclosed in U.S. Pat. No. 3,911,099, Oct. 7, 1975 to Den Foney et al. Another form is a mouthwash concentrate in a unit dosage cup as disclosed in U.S. Pat. No. 4,312,889, Jan. 26, 1982 to Melsheimer. Breath protection microcapsules are disclosed in U.S. patent application Ser. No. 08/003,080 to Stapler et al., filed Jan. 11, 1993, now U.S. Pat. No. 5,300,305 issued Apr. 5, 1994 and U.S. patent application Ser. No. 08/017,944 to Stapler et al., filed Feb. 12, 1993, now U.S. Pat. No. 5,286,496 issued Feb. 15, 1994. All of these references are incorporated herein by reference.

The present inventors have found that by incorporating the breath control/antimicrobial actives into the core of the microcapsule along with organic diluents and a specific sweetener combination, problems associated with other microcapsule executions can be avoided.

The volume limitations inherent in the use of the microcapsules of the present invention requires careful selection of the amount and type of materials contained therein. Without being limited by theory, it has been discovered that the use of a specific sweetener component in the present invention provides increased actual and/or perceived sweetness as well as improving the sweetness perception in the oral cavity. This combination of certain specific sweeteners provides an optimized sweetness profile and/or sweetness intensity in the microcapsules of the present invention.

It is therefore an object of the present invention to provide improved microcapsules.

It is another object of the present invention to provide microcapsules which provide improved breath control and reduce oral bacteria having an improved sweetness profile.

It is still another object of the present invention to provide improved methods of providing breath control and reducing oral bacteria.

These and other objects will become more apparent from the detailed description which follows.

SUMMARY OF THE INVENTION

The present invention in one of its aspects relates to improved microcapsules which contain a sweetener component and breath control actives/antimicrobials in the core of the microcapsule along with an organic diluent and, optionally, in the shell of the microcapsule.

All percentages and ratios used herein are by weight unless otherwise specified. Additionally, all measurements are made at 25° C. unless otherwise specified.

DETAILED DESCRIPTION OF THE INVENTION

The essential as well as optional components of the capsules of the present invention are described in the following paragraphs.

Capsule Shell Material

The shell material of the microcapsules of the present invention can be any materials which are suitable for ingestion as well as retention in the oral cavity. Materials which are suitable include gelatin, polyvinyl alcohols, waxes, gums, sucrose esters and sugar candy type materials used in cough drops and mints, for example.

The shell material is used to form any of a wide variety of shapes such as spheres, oblong shapes, disks, puffed squares and cylinders. The shell thickness is preferably in the range of about 30 um to about 2 mm, preferably from about 70 um to about 150 um. If the microcapsules are spherical, the particle diameter is generally in the range of from about 2 mm to about 9 mm, preferably from about 3 mm to about 7 mm.

Breath Control Agents/Antimicrobials Present in the Core and in the Shell Material The breath control agents used in the cores of the microcapsules include quaternary ammonium salts such as pyridinium salts (e.g., cetyl pyridinium chloride), domiphen bromide, other cationic materials such as chlorhexidine salts, zinc salts and copper salts. Other organic agents such as triclosan and other noncationic water insoluble agents are also useful herein. Such materials are disclosed in U.S. Pat. No. 5,043,154, Aug. 27, 1991, incorporated by reference herein.

These breath control/antimicrobial agents are used in an amount of from about 0.001% to about 2%, preferably from about 0.005% to about 1% of the total core contents.

Dispersed within the shell material may be the same agents at the same concentrations.

Diluents for Use in Microcapsule Core

The solubilizing agent for the breath control/antimicrobial agents used in the cores of the present microcapsules can be any of a number of materials. Preferred are oils such as corn, olive, rape-seed, sesame, peanut or sunflower. Other preferred materials are triglycerides such as Captex 300 and polyethylene glycols such as PEG 400. These are used in an amount of from about 20% to about 80%, preferably from about 35% to about 70% of the total capsule weight.

Sweetener Component

The sweetener component of the present invention is a sweetener mixture having an improved sweetness intensity and/or profile comprising:

(a) acetosulfame and (b) a second artificial sweetener selected from the class of the aspartyl peptide esters, the sulfamate sweeteners, the sulfimide sweeteners, the dihydrochalcone sweeteners and the ammoniated glycyrrhizins and mixtures thereof.

These sweetener combinations are more fully described in U.S. Pat. No. 4,158,068 to Von Rymon Lipinski et al., issued Jun. 12, 1979, incorporated by reference herein.

Acetosulfame is a potassium salt. In principle it could be replaced by other non-toxic water-soluble salts, especially the sodium and calcium salt of 3,4-dihydro-6-methyl-1,2,3-oxathiazine-4-one-2,2-dioxide, but these salts do not bring about any advantages in comparison with the potassium salt.

The most important representatives of the second (b) sweetener classes are mainly the aspartyl phenyl alanine methyl ester (an aspartyl dipeptide ester) and the non-toxic water-soluble salts, especially the sodium and calcium salt, of cyclohexyl sulfamic acid (sulfamate sweeteners), saccharin and its non-toxic water-soluble salts, especially saccharin-Na (sulfimide sweeteners), the neohesperidin and naringine dihydrochalcones (dihydrochalcone sweeteners) and the ammoniated glycyrrhizins, especially monoammononium glycyrrhizin. One or more of these sweetener types may be mixed with acetosulfame.

The components of the mixture (a) and (b) can be mixed in any possible ratio; however, they are preferably mixed in a ratio inverse to their sweetening powers. The sweetening powers are generally determined in comparison with saccharose, for example, in the manner described in the journal "Chemie in unserer Zeit", pages 142–145 (1975). The following weight ratios of the sweetener components have found to be advantageous:

acetosulfame/aspartyl phenyl alanine methyl ester in a ratio of 1:10 to 10:1, especially of about 3:1 to 1:2.
acetosulfame/sodium cyclamate in a ratio of about 3:1 to 1:12, especially of about 1:2 to 1:12.
acetosulfame/saccharin-Na in a ratio of about 1:2 to 10:1, especially of about 1:1 to 8:1, preferably 1:1 to 3:1.
acetosulfame/neohesperidin-dihydrochalcone in a ratio of about 5:1 to 20:1, especially of about 8:1 to 25:1.

Preferred for use in the microcapsule core is a sweetener component comprising acetosulfame/saccharin-Na/aspartyl phenyl alanine methyl ester and more preferably further comprising monoammononium glycyrrhizin.

Also useful in either the core or shell of the microcapsules are additional sweeteners such as caloric sweeteners, e.g., sucrose, d-fructose and d-xylose, the amino acid sweeteners such as glycine as well as the glycosides such as stevioside.

While the sweetener component of the present invention is generally contained in the core of the microcapsule, it can be contained in the shell and preferably is in both the core and the shell of the microcapsule. Most preferred for use in the microcapsule shell is a mixture of acetosulfame/saccharin-Na/aspartyl phenyl alanine methyl ester, especially in a ratio of about 28:6:1. Without being limited by theory, it is believed that the use of the high potency sweetener component of the present invention in the shell provides an immediate sweet taste when the microcapsule enters the oral cavity, thereby improving the sweetness profile and sweetness perception as well as overall taste perception (including taste coverage) of the microcapsule.

Additional Agents Suitable for Use in the Core of Capsule

The core of the microcapsules of this invention may contain any number of additional materials to provide additional efficacy and/or sensory perceptions. Such agents may include flavoring agents such as thymol, eucalyptol, menthol, methyl salicylate or witch hazel. These agents are used in an amount of from about 0.1% to about 25%, preferably from about 5% to about 15% of the total capsule weight.

In addition, a variety of sweetening agents such as sugars, corn syrups, saccharin or aspartame may also be included in the core. These agents are used in an amount of from about 0.1% to about 5%, preferably from about 0.35% to about 1.5% of the total capsule weight.

Method of Manufacture:

The capsules of the present invention can be made using a variety of techniques. One method is described after the following examples.

Industrial Applicability:

The capsules of the present invention are used by placing the capsules into the mouth and retaining them therein for a period sufficient to provide the desired effect.

The following examples further describe and demonstrate preferred embodiments within the scope of the present invention. The examples are given solely for the purposes of illustration and are not to be construed as illustrative of limitations of this invention. Many variations thereof are possible without departing from the invention's spirit and scope.

EXAMPLES 1–5

The following compositions/capsules are representative of the present invention.

| Component | Weight % | | | | |
|---|---|---|---|---|---|
| | 1 | 2 | 3 | 4 | 5 |
| Gelatin | 9.840 | 10.206 | 8.345 | 9.332 | 9.345 |
| Sorbitol Solution (70% Aqueous, Ex. 1–2; Crystalline, Ex. 4–5) | 3.616 | 4.718 | — | 2.941 | 2.560 |
| Saccharin | 0.418 | 0.423 | 0.542 | 0.460 | 0.548 |
| Acetosulfame | 0.695 | 0.702 | 1.626 | 0.779 | 1.321 |
| Aspartyl phenyl alanine methyl ester | 0.495 | 0.500 | — | 0.577 | 0.397 |
| Monoammononium glycyrrhizin | 0.027 | 0.300 | — | 0.027 | 0.040 |
| Neohesperidin dihydrochalcone | 0.020 | 0.020 | — | — | — |
| FD&C Blue #1 | 0.010 | 0.010 | 0.020 | 0.015 | 0.015 |
| FD&C Yellow #5 | 0.005 | 0.005 | — | — | — |
| Captex 300[1] | 8.352 | 8.453 | 71.925 | 69.260 | 8.448 |
| Flavor | 7.158 | 7.240 | 7.247 | 12.112 | 7.239 |
| Citric Acid | — | — | — | 0.259 | — |
| Cetyl Pyridinium[2] chloride | 0.675 | — | — | — | 0.135 |
| Domiphen Bromide | 0.075 | — | — | — | 0.015 |
| Propylene Glycol | 2.017 | — | 3.025 | — | 2.040 |
| Glycerin | 0.270 | — | 4.385 | 0.273 | 0.404 |
| Chlorhexidine | — | 0.120 | — | — | — |
| ZnCl$_2$ | — | — | 0.025 | — | — |
| Sodium Lauryl Sulfate | — | — | 0.300 | — | — |
| Triclosan | — | — | — | 0.280 | — |
| Polyethylene glycol 400 | 29.522 | 31.900 | — | — | 29.703 |
| Sucrose Acetate Isobutyrate | 33.408 | 33.785 | — | — | 33.790 |

-continued

| Component | Weight % | | | | |
|---|---|---|---|---|---|
| | 1 | 2 | 3 | 4 | 5 |
| Water | 3.397 | 1.618 | 2.560 | 3.685 | 4.000 |

[1] Captex 300 is a triglyceride supplied by Capitol City Product, Columbus, Ohio.
[2] This amount includes that in the gelatin shell as well as in the core.

The above compositions are prepared by mixing the components of the core in one container and the components of the shell(s) in another container. The shell(s) materials are heated to provide a fluid medium. The core and shell(s) materials are then pumped separately to a two or three fluid nozzle submerged in an organic carrier medium. The capsules formed are allowed to cool and stiffen. They are then dried and separated for further handling.

In the above compositions any of a wide variety of other shell materials, breath control agents, sweeteners as well as other components may be used in place of or in combination with the components listed above. These are listed on pages 2 through 5.

What is claimed is:

1. A microcapsule suitable for reducing oral bacteria and providing breath protection comprising a shell material suitable for use in the mouth and ingesting and a core composition comprising:
   (a) cetyl pyridium chloride; and
   (b) a sweetener component comprising:
      (1) acetosulfame; and
      (2) a second artificial sweetener selected from the class of the aspartyl peptide esters, the sulfamide sweeteners, the sulfimide sweeteners, the dihydrochalocone sweeteners and the ammoniated glycyrrhizins and mixtures thereof
   wherein the ratio by weight of (1) to (2) is from about 1:15 to about 15:1.

2. A microcapsule according to claim 1 wherein the second artificial sweetener is selected from the group consisting of aspartyl phenyl-alanine methyl ester, the sodium salt of cyclohexyl sulfamic acid, the sodium salt of saccharin, and neohesperidin-dihydrochalcone and mixtures thereof.

3. A microcapsule according to claim 2 wherein the shell material is selected from the group consisting of polyvinyl alcohol, gelatin, waxes, gums and sugar candies.

4. A microcapsule according to claim 3 wherein the microcapsule is in the form of a sphere, oblong, disk, a puffed square, or a cylinder and the breath control agent is a quaternary ammonium salt.

5. A microcapsule according to claim 4 wherein the microcapsules are in the form of spheres.

6. A microcapsule according to claim 5 wherein the microcapsules are from about 2 mm to about 9 mm in diameter and the shell wall thickness is from about 30 um to about 2 mm.

7. A microcapsule according to claim 6 wherein the shell material is gelatin.

8. A microcapsule according to claim 7 wherein the microcapsules are made using a three fluid nozzle.

9. A microcapsule according to claim 3 wherein the sweetener component is incorporated into the microcapsule core.

10. A microcapsule according to claim 9 wherein the sweetener component comprises a mixture of acetosulfame, saccharin-Na, aspartyl phenyl alanine methyl ester and monoammononium glycyrrhizin.

11. A microcapsule according to claim 3 wherein the sweetener component is incorporated into the microcapsule shell.

12. A microcapsule according to claim 11 wherein the sweetener component comprises a mixture of acetosulfame, saccharin-Na, and aspartyl phenyl alanine methyl ester.

13. A method of reducing oral bacteria or breath odor in the mouth wherein capsules according to claim 1 are placed in the mouth of a human or lower animal in need of reducing breath odor or bacteria and left therein for a time sufficient to provide a benefit.

14. A method according to claim 9 wherein the microcapsule shell is made of gelatin.

15. A method according to claim 10 wherein the breath control/antimicrobial active is selected from the group consisting of cetyl pyridinium chloride, domiphen bromide and mixtures thereof.

16. A method according to claim 11 wherein the microcapsule is in the form of a sphere.

* * * * *